United States Patent [19]
Fitch

[11] Patent Number: 5,540,089
[45] Date of Patent: Jul. 30, 1996

[54] FERROUS PARTICLE COLLECTION APPARATUS

[75] Inventor: James C. Fitch, Tulsa, Okla.

[73] Assignee: Diagnetics, Inc., Tulsa, Okla.

[21] Appl. No.: 241,624

[22] Filed: May 12, 1994

Related U.S. Application Data

[63] Continuation-in-part of Ser. No. 210,871, Mar. 17, 1994.

[51] Int. Cl.$^6$ .............................. B03C 1/02; B03C 1/035
[52] U.S. Cl. ................... 73/61.42; 73/53.07; 73/61.72; 210/695; 210/222; 210/223; 356/38; 356/70; 324/204
[58] Field of Search .................. 73/61.42, 61.91, 73/61.72, 61.73, 865.5, 53.07; 210/695, 222, 223, 294, 295, 332, 333.01; 95/27, 28; 96/1, 2, 3; 324/204; 356/30, 70, 72, 336; 209/8, 214

[56] References Cited

U.S. PATENT DOCUMENTS

| | | | |
|---|---|---|---|
| 2,105,851 | 1/1938 | Vobach et al. | 73/53.07 |
| 2,464,628 | 3/1949 | Willard | 210/222 X |
| 4,047,814 | 9/1977 | Westcott | 73/53.07 X |
| 4,375,407 | 3/1983 | Kronick | 209/214 X |
| 4,500,839 | 2/1985 | Jones et al. | 324/204 |
| 4,686,469 | 8/1987 | Lewis | 324/204 |
| 5,053,344 | 10/1991 | Zborowski et al. | 356/38 X |
| 5,122,269 | 6/1992 | De Reuver | 210/222 |

FOREIGN PATENT DOCUMENTS

| | | | |
|---|---|---|---|
| 591851 | 1/1934 | Germany . | |
| 2219405 | 9/1989 | United Kingdom . | |
| 8703368 | 6/1987 | WIPO | 73/53.07 |

Primary Examiner—Hezron E. Williams
Assistant Examiner—Michael J. Brock
Attorney, Agent, or Firm—Head & Johnson, P.A.

[57] ABSTRACT

An apparatus and a method to remove and collect ferrous particles from a fluid for ferrous particle analysis. In one embodiment, the apparatus includes a holder chamber and a removable examination slide within the chamber. A magnet induces a magnetic field at the examination slide. A portion of the fluid is passed over the slide in order for the magnetic field to retain ferrous particles on the slide. Thereafter, the slide can be removed from the holder chamber for ferrographic analysis.

8 Claims, 6 Drawing Sheets

FERROUS PARTICLE COLLECTION APPARATUS

CROSS-REFERENCE OF APPLICATION

This is a continuation-in-part application Ser. No. 08/210,871 filed Mar. 17, 1994, entitled "Ferrous Particle Counter Removal Device" which is incorporated herein by reference.

BACKGROUND OF THE INVENTION

1. Field of the Invention

The present invention relates to a method and apparatus to remove and collect ferrous particles from a fluid for ferrous particle analysis. In particular, the present invention relates to a method and apparatus to remove ferrous particles that will operate in conjunction with various contaminant measurement devices and particle counters.

2. Prior Art

Analysis of the fluid in a fluid system is important in recognizing the symptoms of impending machine failure.

The presence of excessive amounts of wear and cavitation debris in a fluid system are tell-tale signs of an impending component failure. Maintenance should ideally be scheduled before harm to other components and catastrophic failure results. Predictive maintenance or condition monitoring is, then, a way to achieve cost savings on equipment and labor expenses.

There are numerous ways to determine solid particle contamination in a fluid system although many of these determine total solid contamination which includes dirt, dust and other debris. It is often desirable to determine the size, the number, and the composition of ferrous particles in the fluid system.

The traditional ways to evaluate the presence of wear metal are by spectrographic elemental analysis, ferrographic analysis, and various magnetic concentration detectors.

In ferrography, ferrous particles are magnetically deposited on a laboratory slide and viewed under a microscope. Analytical ferrography can be useful as a supplemental tool to localize faults and interpret wear processes.

Spectrographic analysis can be used to establish and quantify the presence of wear metals and additives in fluids. This may be accomplished through atomic emission, atomic absorption, or inductive coupled plasma spectrometry. The technique is limited in its ability to count and size particles and is unable to access elements from particles larger than 8 microns.

Magnetic concentration detectors use a magnetic technique to estimate ferrous levels as a density (for example, ppm, or umg/ml) but are unable to count and size ferrous particles.

There remains a need to provide a device and a method for determining the ferrous particle contamination in the field and laboratory specifically as a measure of count and size.

It is additionally advantageous to provide a method and apparatus to determine ferrous particle contamination in a fluid by probing on or connecting to a fluid system.

It is additionally advantageous to provide a method and apparatus to determine ferrous particle contamination that will operate in conjunction with various solid contamination measurement devices and particle counters.

It is also advantageous to provide a method and an apparatus to determine ferrous particle contamination in-line in a fluid system.

It is, therefore, a principal object and purpose of the present invention to determine ferrous particle sizes and counts in a fluid.

It is an additional object and purpose of the present invention to dynamically determine ferrous particle sizes and counts in a fluid in the field.

It is a further object and purpose of the present invention to determine ferrous particle sizes and counts in-line in a fluid system.

It is a further object and purpose of the present invention to remove and collect ferrous particles from a fluid in order to perform ferrous particle analysis.

It is a further object and purpose of the present invention to remove and collect ferrous particles for ferrography in conjunction with other contamination measurement devices and operations.

It is a further object and purpose of the present invention to provide a portable apparatus and procedure to remove ferrous particles from a fluid system and deposit on a slide or screen while in the field.

SUMMARY OF THE INVENTION

The present invention provides an apparatus and a method to remove and collect ferrous particles from a fluid in order to perform ferrous particle study and analysis.

The apparatus includes an inlet having a threaded port which is in fluid communication with a holder chamber. The holder chamber is formed from at least two segments, a first segment threadably connected to a second segment. Access to the holder chamber is thus provided by threading the segments from each other.

In one embodiment, a removable examination slide is disposed in the holder chamber substantially perpendicular to the flow of fluid coming from the inlet. The flow of fluid is directed to the center of the round examination slide and then radially outward.

Also within the holder chamber is a permanent magnet which induces a magnetic field at the examination slide. The magnet may be secured to the examination slide by a clip.

The holder chamber is also in fluid communication with an outlet so that fluid may pass into, through and out of the holder chamber.

A portion or sample of the fluid from the fluid system along with the entrained ferrous particles are directed through the apparatus. The ferrous particles are retained on top of the slide by the magnetic force. Thereafter the examination slide which is clipped to the magnet is removed and allowed to dry. The slide may be directly used under a microscope for ferrographic analysis.

DETAILED DESCRIPTION OF THE PREFERRED EMBODIMENTS

Figure 1:
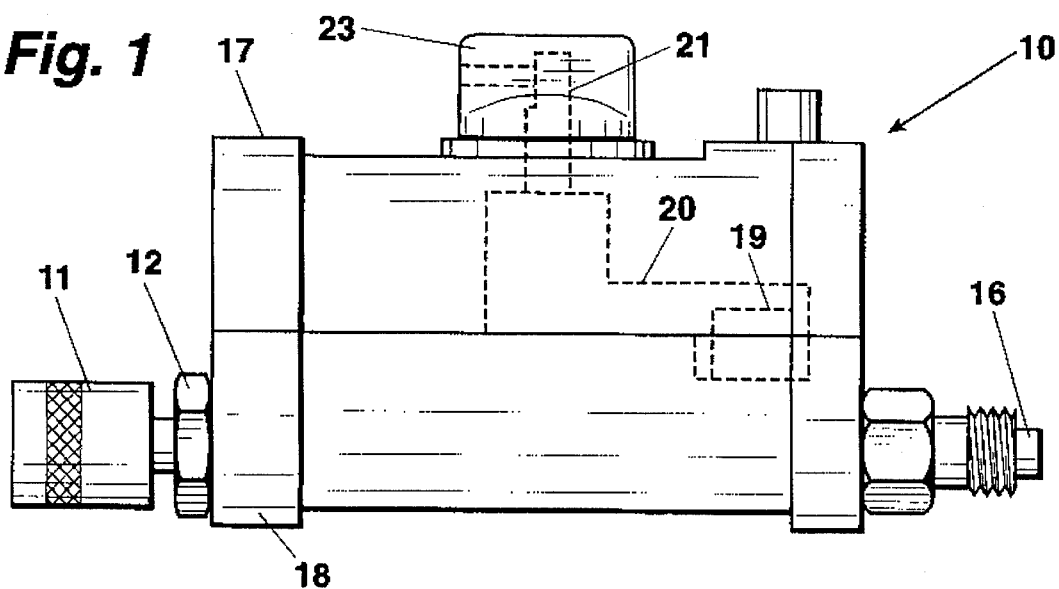
FIG. 1 is an elevation view of an apparatus for determining ferrous particle contamination in a fluid constructed in accordance with the present invention.
Figure 2:
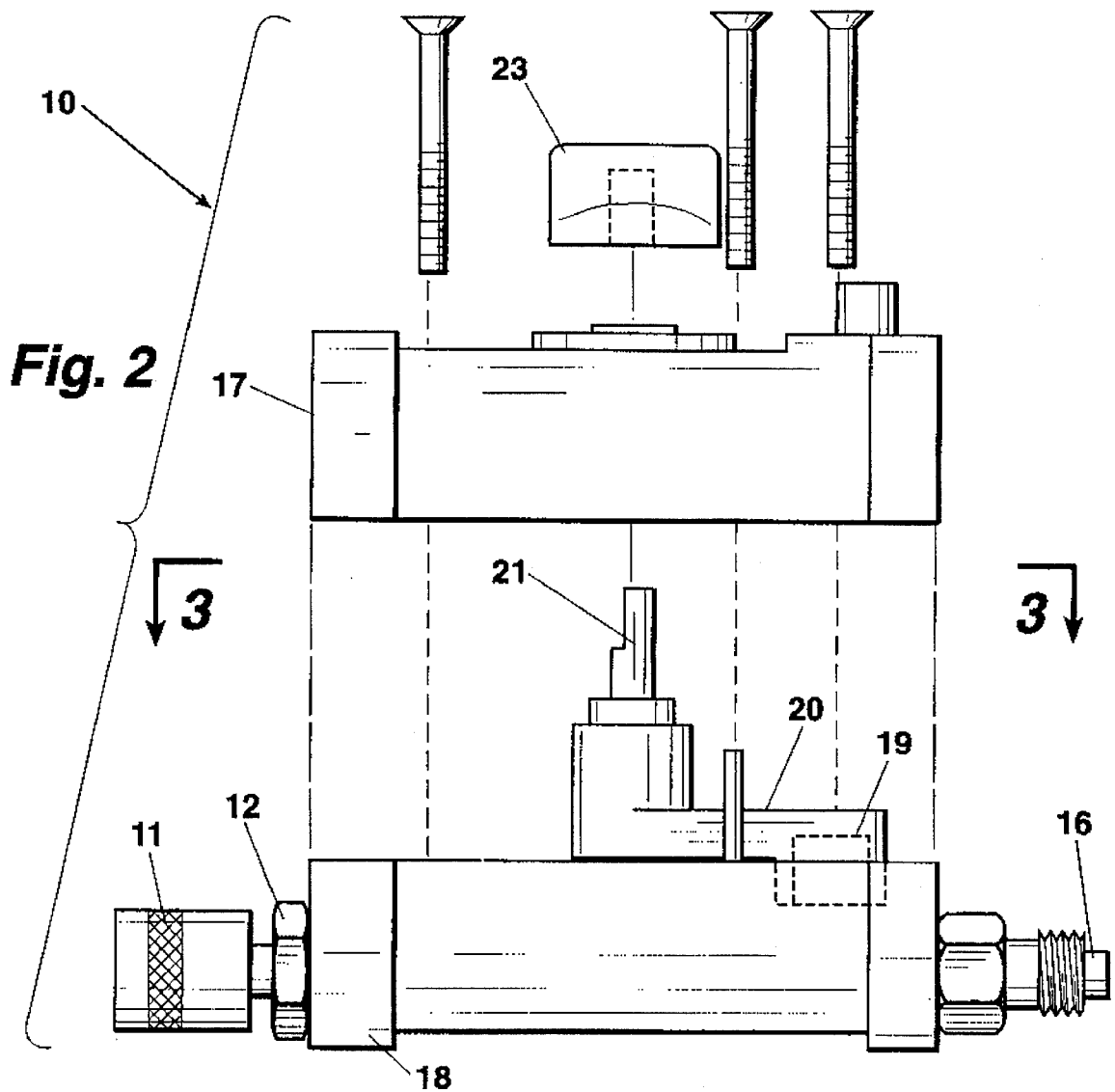
FIG. 2 is an exploded view of the ferrous particle contamination apparatus as shown in FIG. 1.

Referring to the drawings in detail, FIG. 1 is an elevation view of a device 10 used in determining ferrous particle counts in a fluid. FIG. 2 is an exploded view of the device 10 shown in FIG. 1. The device is used with a solid particle count measurement apparatus to be described herein.

The invention includes a sampling probe 11 having internal threads which will connect to a port (not shown in FIG. 1–4) on a fluid system, such as a hydraulic system. The present invention has numerous applications in various fluid systems. In this way, the device 10 may be used in-line with a fluid system.

The sampling probe 11, is, in turn, connected to an adapter 12. The sampling probe 11 terminates in an end having external threads which mate with internal threads in adapter 12.

Figure 3:
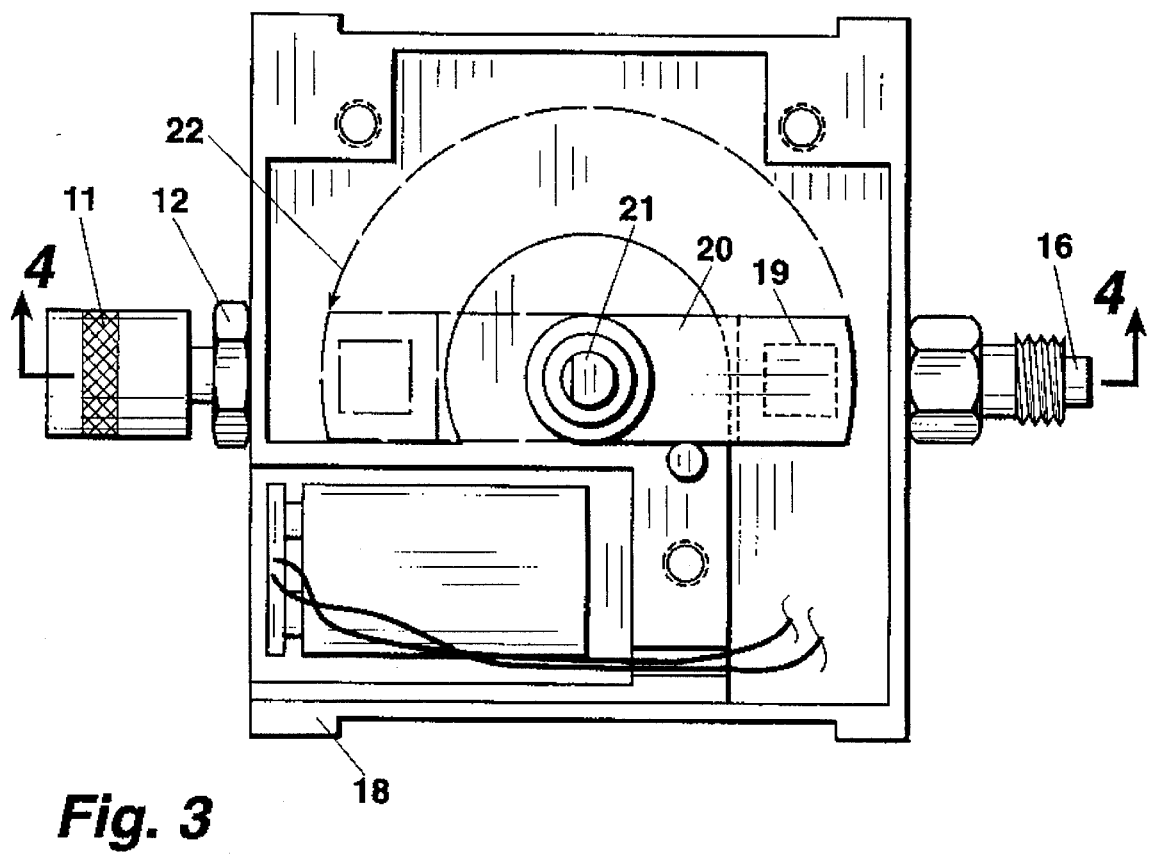
FIG. 3 is a sectional view of the ferrous particulate contamination apparatus taken along section line 3—3 of FIG. 2.
Figure 4:
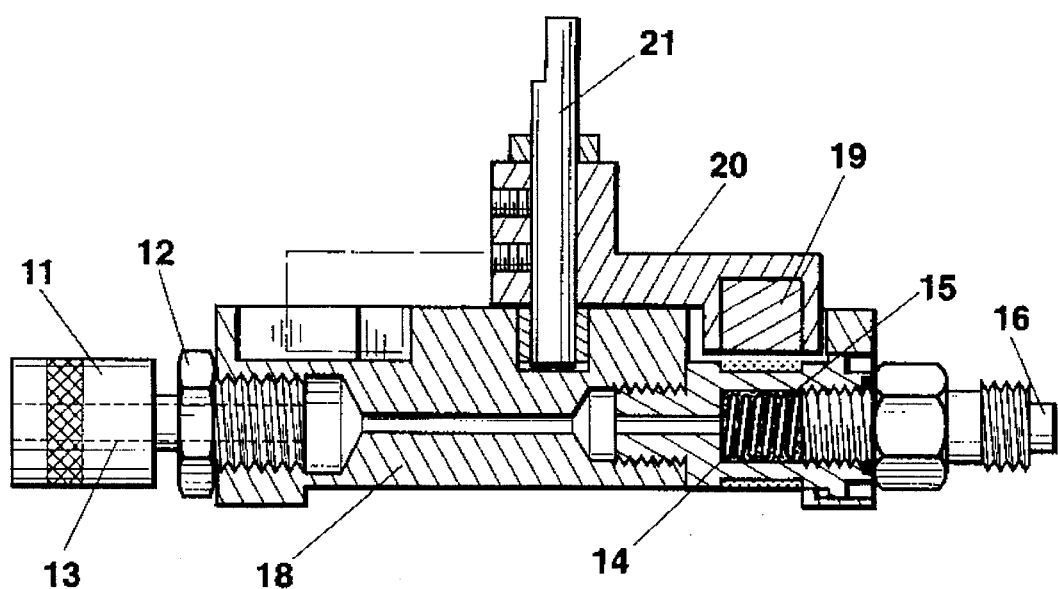
FIG. 4 is a sectional view of the ferrous particle contamination apparatus taken along section line 4—4 of FIG. 3.

FIG. 3 is a sectional view taken along section line 3—3 of FIG. 2 while FIG. 4 is a sectional view taken along section line 4–4 of FIG. 3.

As best seen in FIG. 4, the sampling probe 11 and adapter 12 each having axial openings which together form a passageway 13 from the fluid system into a separator chamber 14. A source of fluid from the fluid system to be monitored is, thus, supplied.

The separator chamber 14 is filled with a ferrous mesh media 15. While a mesh media is employed, it will be understood that other ferrous media, such as single screens or wafers might be used. The separator chamber 14 is, in turn, in fluid connection with a test port 16. When a contamination measurement is not being taken, the test port 16 may be closed off by a threaded end (not shown).

Fluid entering the sampling probe 11 from the fluid system is under pressure. It will, thus, be seen that fluid entering the sampling probe 11 will be allowed to pass into and through the device 10.

A housing formed of two halves 17 and 18 surrounds the separator chamber and passage.

A magnet 19, external to the separator chamber, is held by at the end of a radial rotor arm 20. The rotor will rotate about shaft 21 which acts as its axis. The magnet 19 is thus allowed to travel in a radial path shown by arrow 22. The magnet 19 is secured by retained compound and a set screw.

The shaft 21 pass through an opening in the body half 17 and terminates in a knob 23. Rotation of the knob will move the rotor arm and the magnet 19.

The magnet 19 induces a magnetic field which passes through the separator chamber 14 wherein the position in FIGS. 1–4. The ferrous mesh media 15, thus, becomes magnetized. As fluid passes through the separator chamber, ferrous particles are drawn toward and suspended by the media.

Rotating the rotor arm 20 one hundred and eighty degrees (180°) moves the magnetic field from the separator chamber.

While a ½" cube magnet is shown in the embodiment in FIGS. 1–3, other types of permanent magnets may also be employed. It will also be recognized that an electromagnet, that would be activated as desired, could also be used.

The separator chamber 14 is constructed of aluminum or other non-ferrous material so that it will not become magnetized itself. The diameter of the chamber is significantly larger than any of the passages through the device 10. This causes the velocity of fluid in the separator chamber 14 to be reduced from that in the passages. It will, thus, require less magnetic force to pull out and retain ferrous particles from the fluid.

Figure 6:
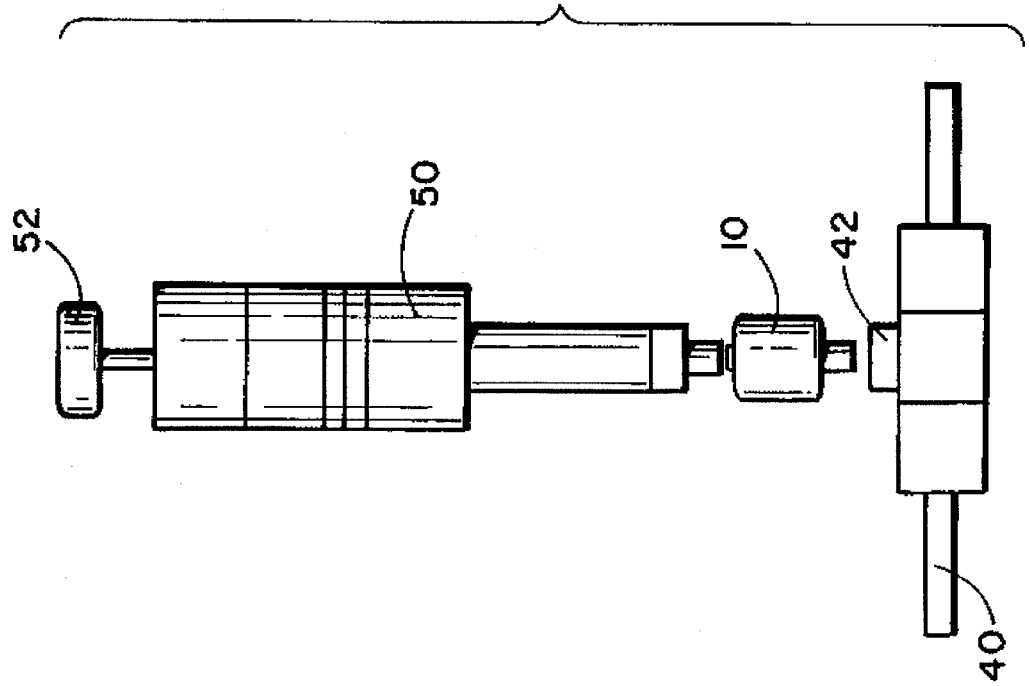
FIGS. 5 and 6 diagrammatically illustrate the process used to determine ferrous particle contamination in a fluid as taught by the present invention.
Figure 5:
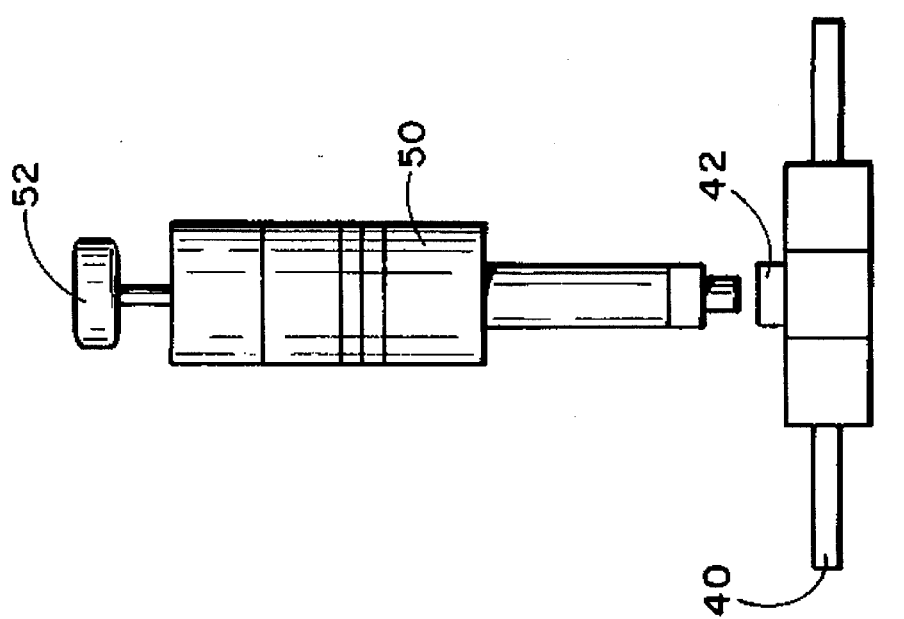

FIGS. 5 and 6 diagrammatically illustrate one process used to determine the ferrous particle contamination level in the fluid. A first measurement reading is taken as illustrated in FIG. 5, followed by a second measurement reading as illustrated in FIG. 6. It will be appreciated that the measurement readings may be taken in reverse order and a comparison made.

Fluid from the system would be directed into and through an inlet line 40 to an inlet port 42 having a threaded connection. A first solid contamination level is determined by measuring the solid particulate contamination in the fluid.

The contamination measurement apparatus 50 includes a test screen to provide mechanical filtration of particulate matter in order to determine solid contamination levels in the fluid. One such measurement apparatus is illustrated in Hodgson et al, U.S. Pat. No. 5,095,740 although many other types of solid contamination measurement devices may be used.

During a measurement test, fluid will pass through the screen leaving particles on the screen's surface. The particles gradually close off available pores and flow through the screen is thereby reduced. On the opposite side of the test screen is a passageway leading to a cylindrical test chamber. A test piston is allowed to move within the test chamber. The test piston is linked to a linear gauge which moves in response to the piston rod. Linear movement of the test piston will, thus, move the linear gauge linearly. Other analytical gauges could be used to track the position of the test rod.

In the measurement stroke, pressurized fluid in the system will be allowed to pass through the test screen and cause the test piston to move. The speed or velocity of the moving test piston is sensed or picked up by the linear gauge and relayed to a data acquisition unit. The test piston rod will slow down as the particulate matter accumulates on the screen. The information on the change in speed of the test piston as the fluid moves is used to determine and calculate the particulate count of contamination in the fluid. By monitoring the change in speed of the piston rod, the level of particulate matter is determined.

A back flush stroke is also included. A handle 52 extends from the device 50 and is connected to the test piston rod. The handle 52 is used to drive the test piston rod and test piston back into the initial position to begin another cycle and begin another test. The back flush stroke forces all of the fluid back in the reverse direction through the screen.

A reading is thereby achieved of all the solid particulate matter in the fluid.

Turning to FIG. 6, a second solid contamination level is determined. The device 10 of the present invention is inserted between the removal device 50 and the fluid system. The sampling probe 11 is threadably connected to the inlet port 42 and the test port 13 is connected to measurement apparatus 50.

As fluid passes through the separator chamber 14 of the ferrous particle removal device 10, any ferrous particles will be drawn to and captured by the wire mesh media 15 which has been induced with a magnetic field.

The fluid thereafter passes into the contamination measurement apparatus or particle counter 50. Accordingly, only non-ferrous particles will pass into the contamination measurement or particle counter apparatus 50. The same procedure as previously described will be performed again in order to determine the non-ferrous contaminants in the fluid.

Thereafter, the total solid contamination is compared to or measured against the non-ferrous solid contamination. The difference between the two is the ferrous contamination level in the fluid.

The size of the ferrous particles in the fluid system may be determined by changing the screen in the contamination measurement apparatus to a different pore size and again taking the two measurements.

The two readings may be delivered to a central processing unit so that the difference is calculated and displayed on a monitor.

It will be appreciated that the process may also be performed in the reverse order. That is, the non-ferrous solid contamination level may be measured first. Thereafter, the total solid contamination level may be measured. Finally, the difference between the two is the level of ferrous contamination in the fluid.

As an alternate process, the ferrous particle counter 10 of the present invention may be left in place juxtaposed between the fluid system and the contamination measurement or particle counter apparatus 50. In order to take the reading of total solid particulate matter, the knob 23 is rotated so that the magnet field is moved away from the separator chamber.

It will also be appreciated that the ferrous particle removal device 10 may be permanently secured to the particle counter 50.

Figure 7:
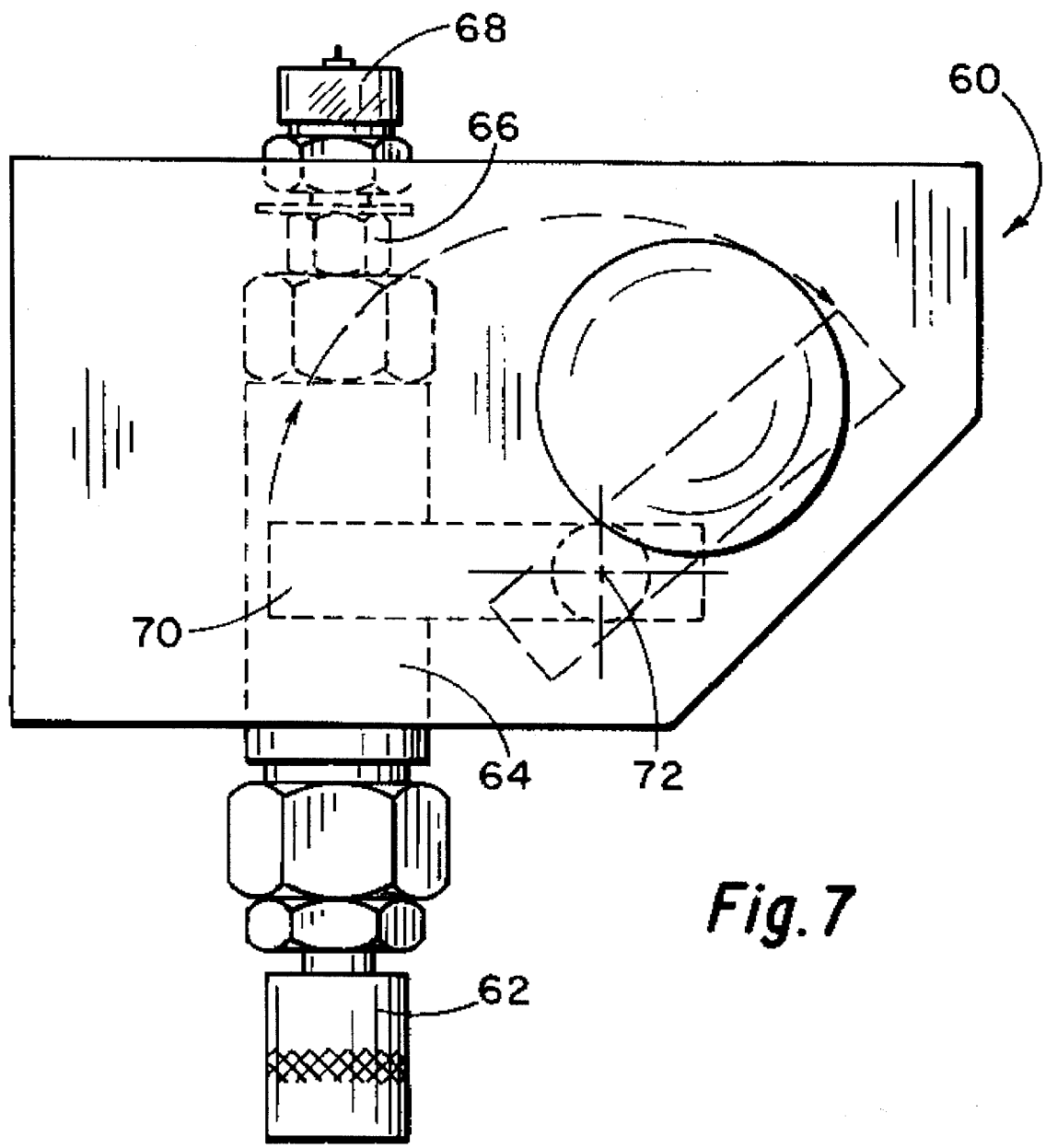
FIG. 7 is a perspective view of an alternate embodiment of an apparatus for determining ferrous particle contamination in accordance with the present invention.

FIG. 7 is an alternate embodiment 60 of the device to measure ferrous particle contamination in the fluid.

A sampling probe 62 is in fluid communication with a separator chamber 64 containing a wire mesh media or other ferrous media that may be magnetized. The apparatus 62 extends to an adapter 66 and terminates in a test port 68.

A magnet item 70 (shown by dashed lines) is used to induce a magnetic field. The magnet is attached to a rotor which pivots about a shaft 72 which provides an axis for rotation. In the first position, the magnet induces a magnetic field in the wire mesh media, thereby providing a magnetic force which attracts ferrous particles as previously described. In the opposite position, the magnetic field of the magnet does not pass into or through the separator chamber. It has been found that rotating the magnet rotor at least 180° about the axis removes the magnetic field from the wire mesh media.

It may also be desirable to not only determine the size and count of ferrous particles in the fluid system, but to remove a sample of the ferrous particles for examination.

Figure 8:
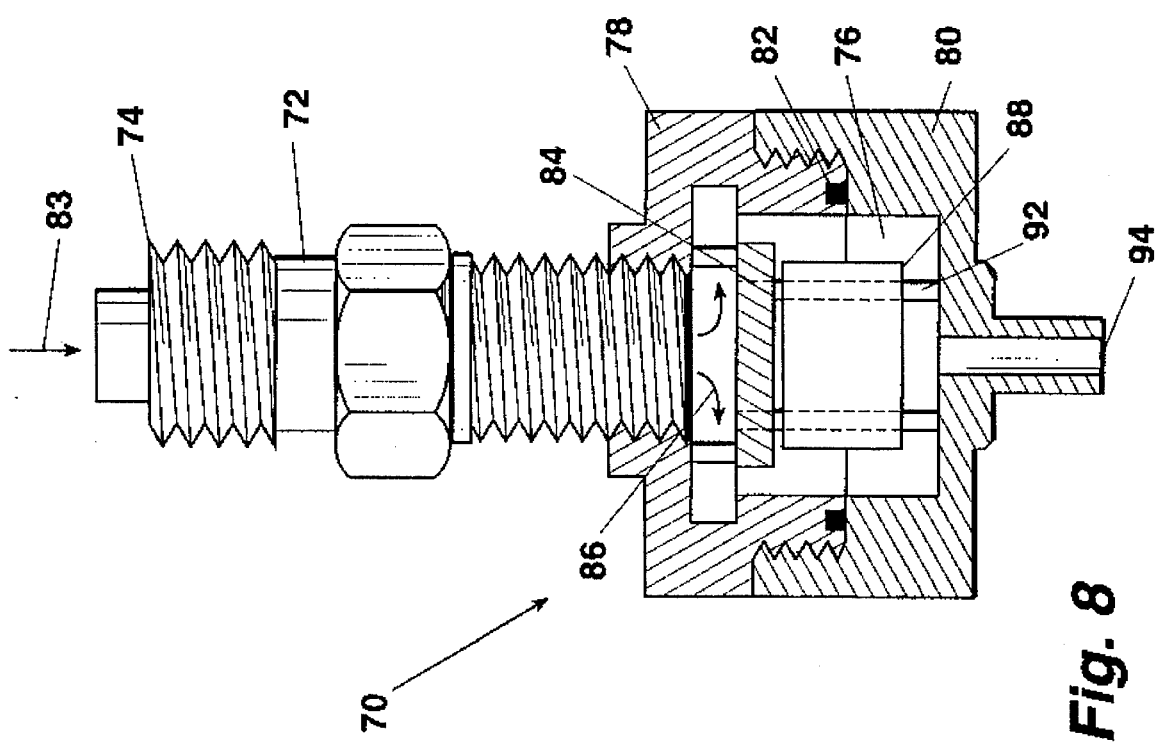
FIG. 8 is a sectional view of an apparatus to remove and collect ferrous particles from a fluid constructed in accordance with the present invention.

FIG. 8 is a partial sectional view of ferrous particle collection apparatus 70 to remove ferrous particles from a fluid for ferrous particle analysis. The apparatus 70 includes an inlet 72 having a threaded port 74 which is in fluid communication with a holder chamber 76. In this manner, a source of fluid from the fluid system to be monitored is, thus, supplied.

The holder chamber 76 is formed from at least two segments, a first segment 78 and second segment 80. The segments are threadably connected with a seal 82 therebetween. Accordingly, the segments may be threaded together to form the fluid tight holder chamber. The segments may be constructed of aluminum or other nonferrous material to avoid interference with the magnetic force to be described. Access to the holder chamber is easily and rapidly gained by unthreading the segments 78 and 80 from each other.

Fluid from the fluid system will be permitted to flow in the direction shown by arrow 83. A removable examination slide 84 is disposed in the holder chamber 76 substantially perpendicular to the flow of fluid coming from the inlet. The fluid is directed to the center of the round examination slide and then radially outward as illustrated by arrows 86.

Also within the holder chamber is a permanent magnet 88. The permanent magnet 88 induces a magnetic field at the examination slide. The magnetic field will pass through the glass examination slide so that ferrous particles will be retained on the top 90 of the examination slide. The magnet may be secured to the slide by a clip 92.

The holder chamber 76 is also in fluid communication with an outlet 94 so that fluid may pass into, through, and out of the holder chamber. The outlet may be directed to a waste receptacle or the like.

Figure 9:
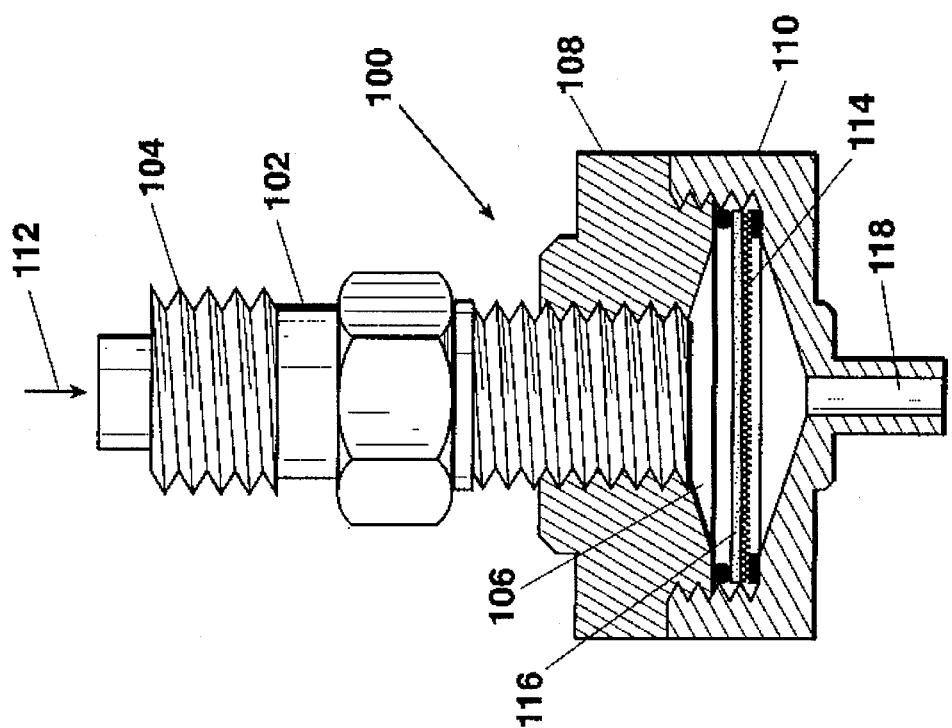
FIG. 9 is a sectional view of an alternative embodiment of an apparatus to remove and collect ferrous particles from a fluid.

FIG. 9 shows an alternate embodiment of an apparatus 100 to remove ferrous particles from a fluid for ferrous particle analysis. The apparatus 100 includes an inlet 102 having a threaded port 104 which is in fluid communication with a holder chamber 106. In this manner, a source of fluid from the fluid system to be monitored is, thus, supplied.

The holder chamber 106 is formed from at least two segments, a first segment 108 threadably connected to a second segment 110. Accordingly, the segments may be threaded together to form the fluid tight holder chamber. Access to the holder chamber is easily and rapidly gained by unthreading segments 108 and 110 from each other.

Fluid from the fluid system will be permitted to flow in the direction shown by the arrow 112. A filter holder 114 is disposed substantially perpendicular to the flow of fluid coming from the inlet. The filter holder 114 in the present embodiment is substantially flat and porous. The filter holder 114 supports a filter, such as a paper filter 116, which will trap ferrous particles and prevent them from the passing through the holder chamber.

The holder chamber 106 is also in fluid communication with an outlet 118 so that fluid may pass into the holder chamber and thereafter pass out of the holder chamber. The outlet may be directed to a waste receptacle or the like.

The apparatus is lightweight, portable and may be connected with various measurement devices.

Figure 10:
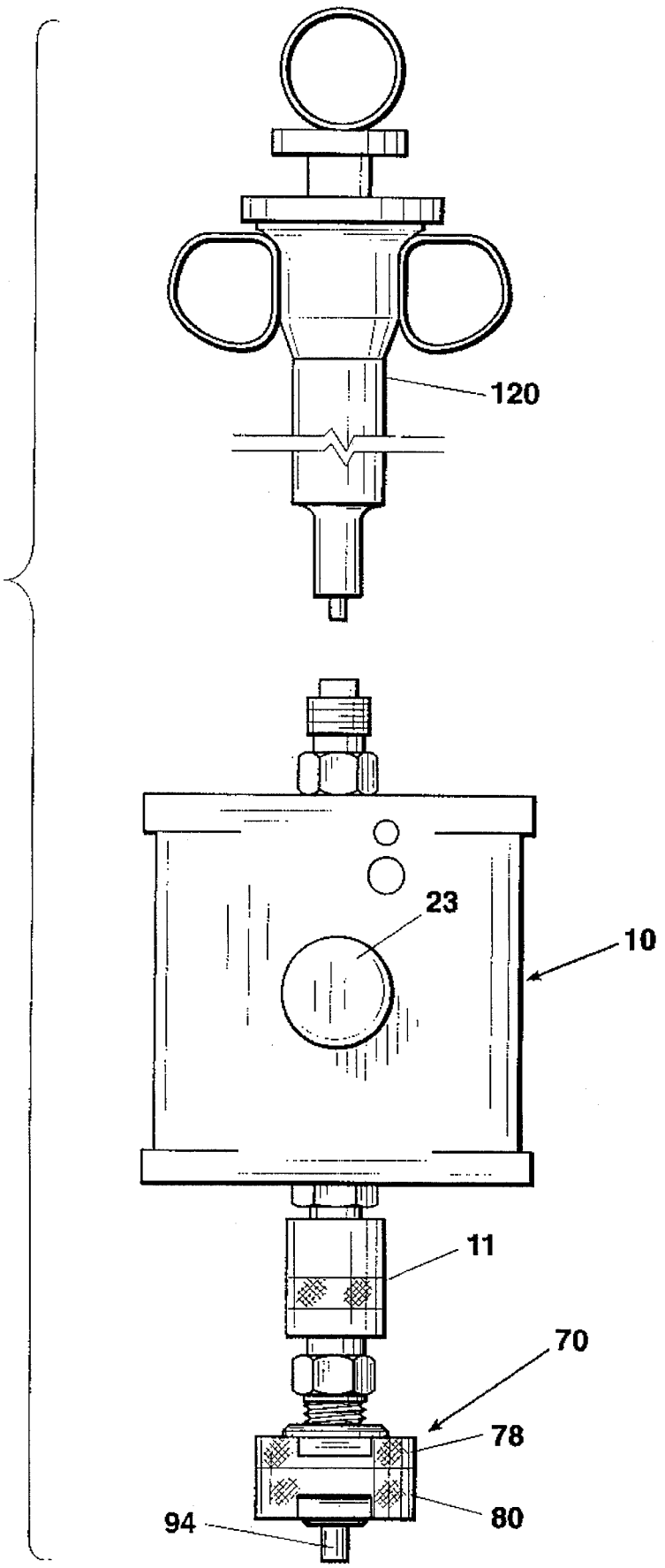
FIG. 10 is an exploded view of the apparatus to remove ferrous particles from a fluid as shown in FIG. 8 attached to the apparatus for determining ferrous particle contamination as shown in FIGS. 1 through 4.

FIG. 10 illustrates one possible arrangement to utilize either apparatus shown in FIGS. 8 or 9 to remove ferrous particles from fluid for particle analysis. The external threads 74 of the inlet 72 may be threadably connected with the sampling probe 11 of the device 10 to determine ferrous particle counts in a fluid.

The ferrous particle collection apparatus 70 may be used in conjunction with the ferrous particle removal device 10 to not only determine the size and count of ferrous particles but to remove ferrous particles from the fluid sample for further study and analysis.

One usage of the apparatus and methods will show the range of possible applications.

With reference to FIG. 6, and continuing reference to FIG. 10, a sample procedure may be appreciated. As seen in FIG. 6, the ferrous particle removal device 10 is attached to the inlet port 42 of the inlet line 40. Initially, a sample of fluid from the fluid system is taken into the ferrous particle removal device 10 and into the particle counter apparatus 50. Thereafter, the device 10 and the particle counter apparatus 50 are removed from the fluid system port 42. The contamination measurement or particle counter apparatus 50 is then separated from the ferrous particle counter device 10.

As seen in FIG. 10, solvent is placed in a syringe 120 which is then connected to the device 10. The solvent will be flushed through and out of the ferrous particle removal device 10 and through and out of the ferrous particle collection apparatus 70. The solvent and ferrous particles are directed to the examination slide and are retained on the top of the slide by the magnetic force. Thereafter, the examination slide which is clipped to the magnet, is removed and allowed to dry. As an optional step, the examination slide may be heated to temper the particles prior to further analysis. The slide may be directly used under a microscope for ferrographic analysis. The presence of wear debris may then be directly observed.

It will be appreciated that a similar procedure can be used with the alternate embodiment 100 shown in FIG. 9, by using a filter instead of an examination slide and magnet combination to collect the ferrous particles.

Various alternate procedures may be employed. One such procedure would be to discharge solvent from the syringe through the ferrous particle removal device while the magnet induces a magnetic force in the ferrous magnetic mesh 15. This will cause the oil or fluid in the system to be flushed out by the solvent yet retain the ferrous particles at the mesh media. Thereafter, the magnet is moved away or turned off so that the magnetic force is removed. The remaining solvent in the syringe is then forced through the ferrous particle removal device 10 and through the collection apparatus 70, depositing ferrous particles on the examination slide 84 without oil or fluid from the system.

The same procedure could be employed by using the alternate embodiment in FIG. 9 with the paper filter.

Whereas, the present invention has been described in relation to the drawings attached hereto, it should be understood that other and further modifications, apart from those shown or suggested herein, may be made within the spirit and scope of this invention.

What is claimed is:

1. An apparatus to remove ferrous particles from a fluid for ferrous particle analysis, which apparatus comprises:

a holder chamber;

a removable examination slide within said chamber;

a magnet to induce a magnetic field at said examination slide; and means to pass a portion of said fluid over said examination slide in order to collect ferrous particles on said slide, so that said slide may thereafter be removed for analysis.

2. An apparatus as set forth in claim 1 including an outlet in fluid communication with said holder chamber and an inlet in fluid communication with said holder chamber, said inlet connected to a separator chamber wherein said ferrous particles are separated from a portion of fluid by inducing a magnetic field.

3. An apparatus as set forth in claim 2 including means to flush said fluid from said separator chamber into and through said holder chamber.

4. An apparatus as set forth in claim 1 wherein said magnet is clipped to said examination slide and is removable therewith.

5. An apparatus to remove ferrous particles from a fluid for ferrous particle analysis, which apparatus comprises:

a holder chamber;

a removal filter within said chamber;

an inlet in fluid communication with said holder chamber, said inlet connected to a separator chamber wherein said ferrous particles are separated from a portion of fluid by inducting a magnetic field; and means to flush said fluid from said separator chamber into and through said holder chamber.

6. A method of removing ferrous particles from a fluid for ferrous particle analysis, which method comprises:

passing a portion of fluid through an inlet in fluid communication with a holder chamber having an examination slide therein and a magnet to produce a magnetic field at said examination slide;

passing said portion of fluid from said holder chamber through a holder chamber outlet; and removing said examination slide from said holder chamber for ferrographic analysis.

7. A method as set forth in claim 6 including the additional steps of:

initially passing a portion of said fluid through a separator chamber;

separating ferrous particles from said fluid portion by inducing a magnetic field at said separator chamber; and removing said magnetic field from said separator chamber prior to passing said portion of fluid through said inlet.

8. A method as set forth in claim 7 wherein said portion of fluid is passed through said holder chamber by forcing a solvent through said separator chamber and through said holder chamber.

* * * * *